United States Patent [19]
Dowdy et al.

[11] Patent Number: 5,038,798
[45] Date of Patent: Aug. 13, 1991

[54] OPTHALMIC DRAPE WITH FLUID COLLECTION POUCH

[75] Inventors: Richard C. Dowdy, Valencia, Calif.; Susan Birch, Lake Forest, Ill.

[73] Assignee: Baxter International Inc., Deerfield, Ill.

[21] Appl. No.: 572,309

[22] Filed: Aug. 23, 1990

Related U.S. Application Data

[63] Continuation of Ser. No. 495,501, Mar. 19, 1990, abandoned.

[51] Int. Cl.$^5$ .............................................. A61B 19/08
[52] U.S. Cl. ...................................... 128/853; 128/849; 604/356
[58] Field of Search ............................... 128/849–856; 604/353–357

[56] References Cited

U.S. PATENT DOCUMENTS

| 3,326,253 | 7/1974 | Larsh et al. |
|---|---|---|
| 3,650,267 | 3/1972 | Anderson. |
| 3,667,458 | 6/1972 | Krebs. |
| 3,791,382 | 2/1974 | Collins. |
| 3,800,790 | 4/1974 | Collins. |
| 3,902,484 | 9/1975 | Winters. |
| 3,910,268 | 10/1975 | Miller. |
| 3,911,912 | 10/1975 | Krebs et al. |
| 3,916,887 | 11/1975 | Kelly. |
| 3,923,052 | 12/1975 | Zoephel. |
| 3,926,185 | 12/1975 | Krzewinski. |
| 3,952,738 | 4/1976 | Krzewinski. |
| 3,955,659 | 5/1976 | Krzewinski. |
| 4,027,665 | 6/1977 | Scrivens. |
| 4,166,461 | 9/1979 | Oliver et al. |
| 4,169,947 | 10/1979 | Morris. |
| 4,275,720 | 6/1981 | Wichman. |
| 4,323,062 | 4/1982 | Canty. |
| 4,378,794 | 4/1983 | Collins. |
| 4,457,026 | 7/1984 | Morris. |
| 4,462,396 | 7/1984 | Wichman. |
| 4,476,860 | 10/1984 | Collins et al. |
| 4,489,720 | 12/1984 | Morris et al. |
| 4,553,539 | 11/1985 | Morris ............................ 128/854 |
| 4,559,937 | 12/1985 | Vinson ......................... 128/853 X |
| 4,598,458 | 7/1986 | McAllester .................... 128/853 |
| 4,869,271 | 9/1989 | Idris .............................. 128/853 |
| 4,890,628 | 1/1990 | Jackson ........................ 128/849 |

Primary Examiner—Robert A. Hafer
Assistant Examiner—Kenny Owens
Attorney, Agent, or Firm—Kay H. Pierce; Paul C. Flattery

[57] ABSTRACT

A surgical ophthalmic drape which is a complete draping system and provides a sterile field and fluid control. The ophthalmic drape includes a main sheet and a fluid pouch. The fluid pouch has a fenestration which is smaller than the main sheet fenestration. The adhesive layer on the bottom of the fluid pouch both secures the pouch to the main sheet and also secures the drape assembly to the patient. The pouch is a folded piece of fluid impervious material with a sealed edge on three sides.

15 Claims, 4 Drawing Sheets

FIG. 2
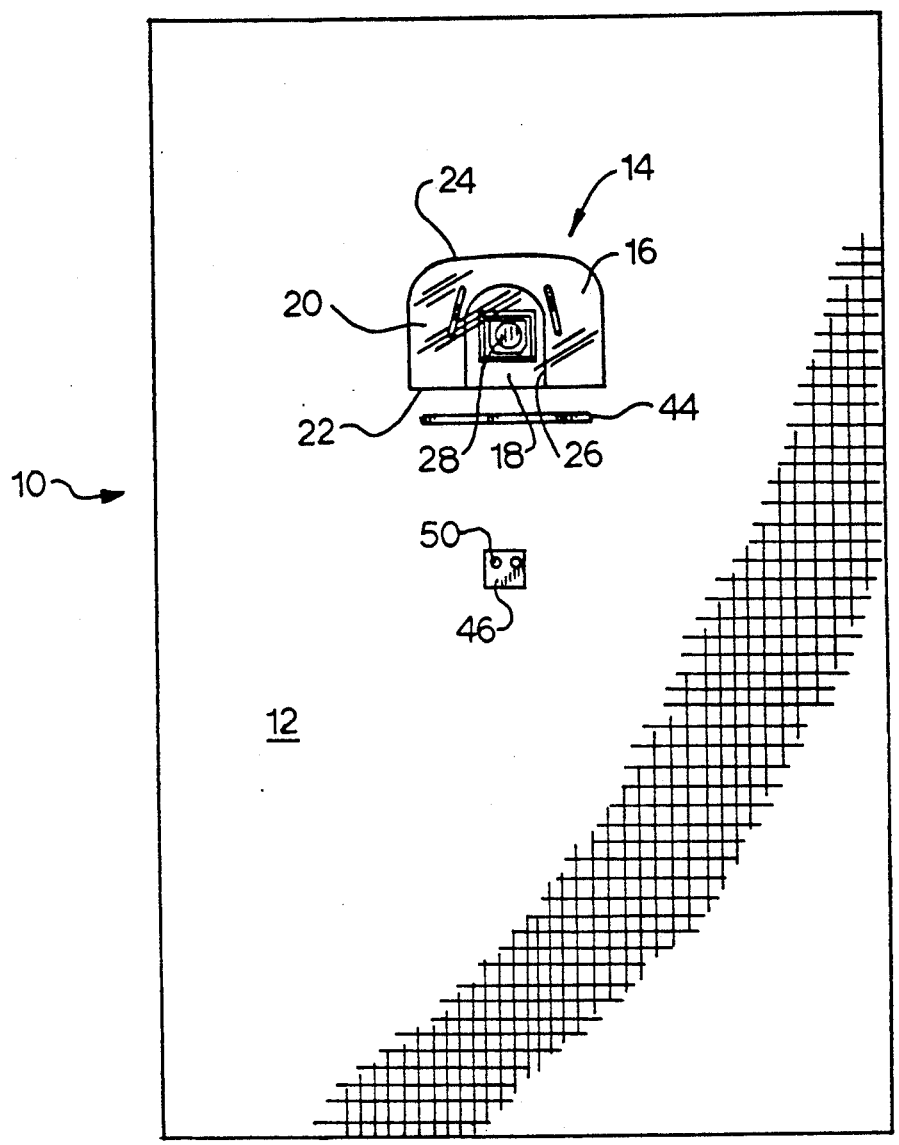
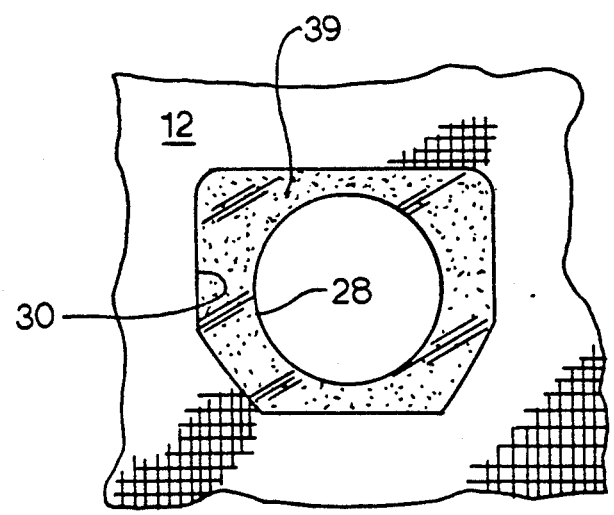
FIG. 6

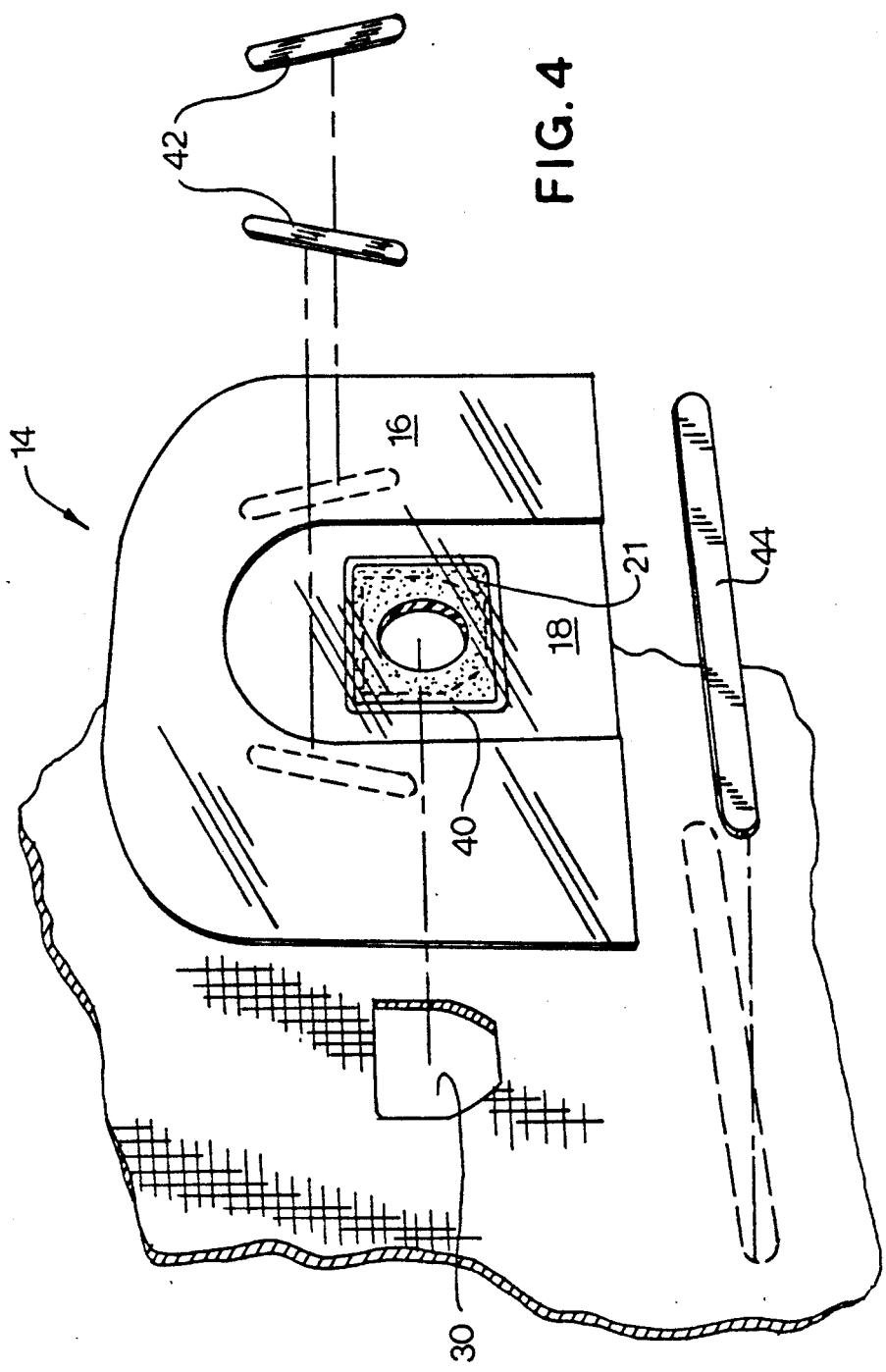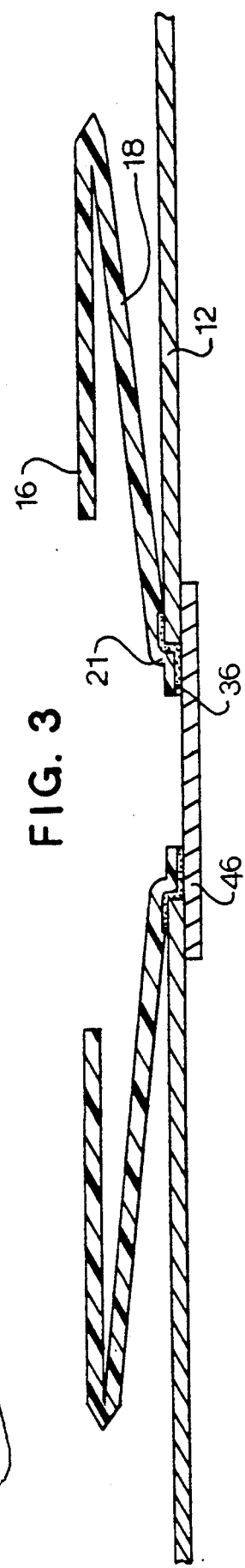

OPTHALMIC DRAPE WITH FLUID COLLECTION POUCH

This is a continuation of application Ser. No. 07/495,501, filed on Mar. 19, 1990 now abandoned.

BACKGROUND OF THE INVENTION

The present invention relates to a drape for use in surgery, especially ophthalmic procedures. More specifically, the present invention relates to an ophthalmic surgical drape having a fluid collection pouch.

For an ophthalmic surgical procedure, hospital personnel previously a used surgical drape system, comprising a main base sheet with a fenestration to allow for draping around the patient's head. A disposable plastic incise drape was then placed over the head and the operative eye, with the ends of the incise drape being folded and placed in a fluid collection pouch attached to the base drape.

This type of multiple drape system require considerable handling and may cause cross-contamination. So drapes were designed incorporating an incise component with an eye fenestration into the base drape to reduce cross-contamination caused by the handling of the various drapes and also to make the use of the drape quicker and easier.

However, these drapes still have a problem adequately controlling the fluid resulting from the operation. Eye drops are generally applied before and during the course of an ophthalmic surgical procedure, so that fluid runoff must always be controlled to maintain an aseptic environment. Even drapes with one pocket on each side of a fenestration have problems because of the path of the fluid is often diagonal or otherwise unpredictable. This causes the drape over the patient's head to become wet with the possibly body fluids, which may be contaminated. When the surgeon leans against the patient, the surgeon's gown becomes soaked with the fluids and may cross-contaminate the patient.

SUMMARY OF THE INVENTION

The present invention provides a surgical drape for use in ophthalmic surgical procedures. The drape includes a base sheet and a fluid impervious fluid collection pouch, having a fenestrations concentric with one another. The pouch fenestration is smaller than the base sheet fenestration.

The fluid collection pouch has a top layer and a bottom layer, with the outside of the bottom layer facing the base sheet. The outside of the pouch bottom layer has an adhesive layer surrounding the fenestration. When the drape is assembled, the adhesive layer adheres the pouch to the main sheet adjacent the main sheet fenestration and also adheres the drape assembly to the patient.

Accordingly, it is an advantage of the present invention to provide a one piece complete draping system providing a sterile field and fluid control.

Another advantage of the present invention is that the drape requires less handling which reduces cross-contamination of the sterile field.

A further advantage of the present invention is that the pouch fenestration adheres to the patient and thus reduces the fluids on the patient beneath the surgical drape.

Moreover, an advantage of the present invention is that when the pouch is horseshoe-shaped to reduce the fluid avoiding the pouch and wetting the base drape.

Another advantage of the present invention is that it provides adjustment strips which allow for gathering of the corners of the pouch to help retain the fluids within the pouch.

Another advantage of the present invention is that the u fluid collection pouch is formed from a single sheet of fluid impervious material and is assembled with one sealing operation.

Moreover, an advantage of the present invention is to provide for a surgical drape which is simple in construction, effective for its purposes and relatively inexpensive to manufacture.

Additional features and advantages are described therein, and will be apparent from, the detailed description of the presently preferred embodiment, and from the drawings.

BRIEF DESCRIPTION OF THE DRAWINGS

FIG. 2 illustrates a top elevational view of the surgical drape of the present invention.

FIG. 3 illustrates a cross-sectional view of the surgical drape taken along lines 3—3 of FIG. 2.

FIG. 4 illustrates a perspective exploded view of the surgical drape.

FIG. 6 illustrates an elevational view of the back of the surgical drape surrounding the main sheet fenestration.

DETAILED DESCRIPTION OF THE PRESENTLY PREFERRED EMBODIMENT

Although the surgical drape described herein was developed specifically for use in ophthalmic surgical procedures, it may be used in other surgical procedures.

Figure 1:
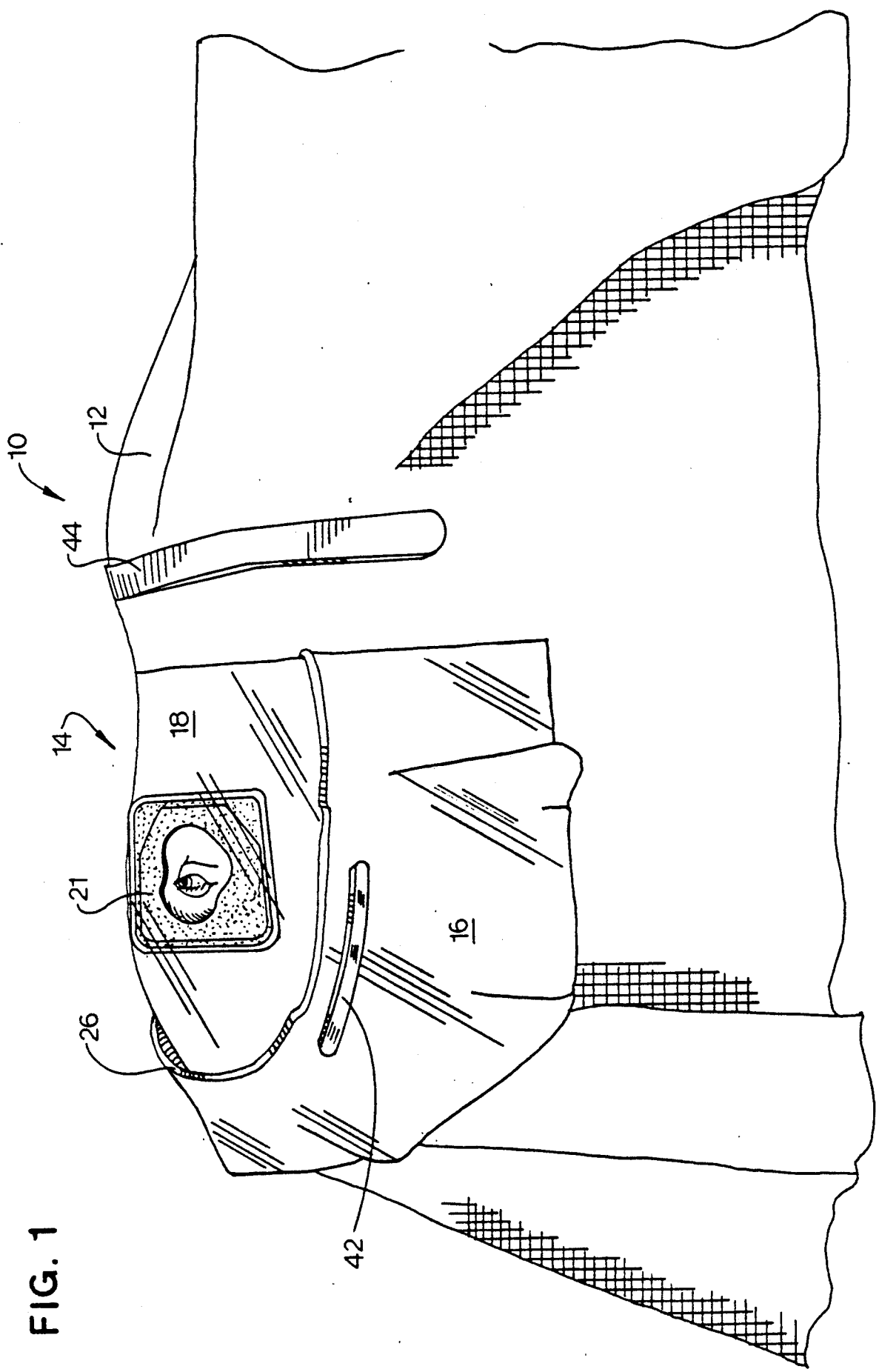
FIG. 1 illustrates a perspective view of the surgical drape of the present invention in use on a patient.
Figure 5:
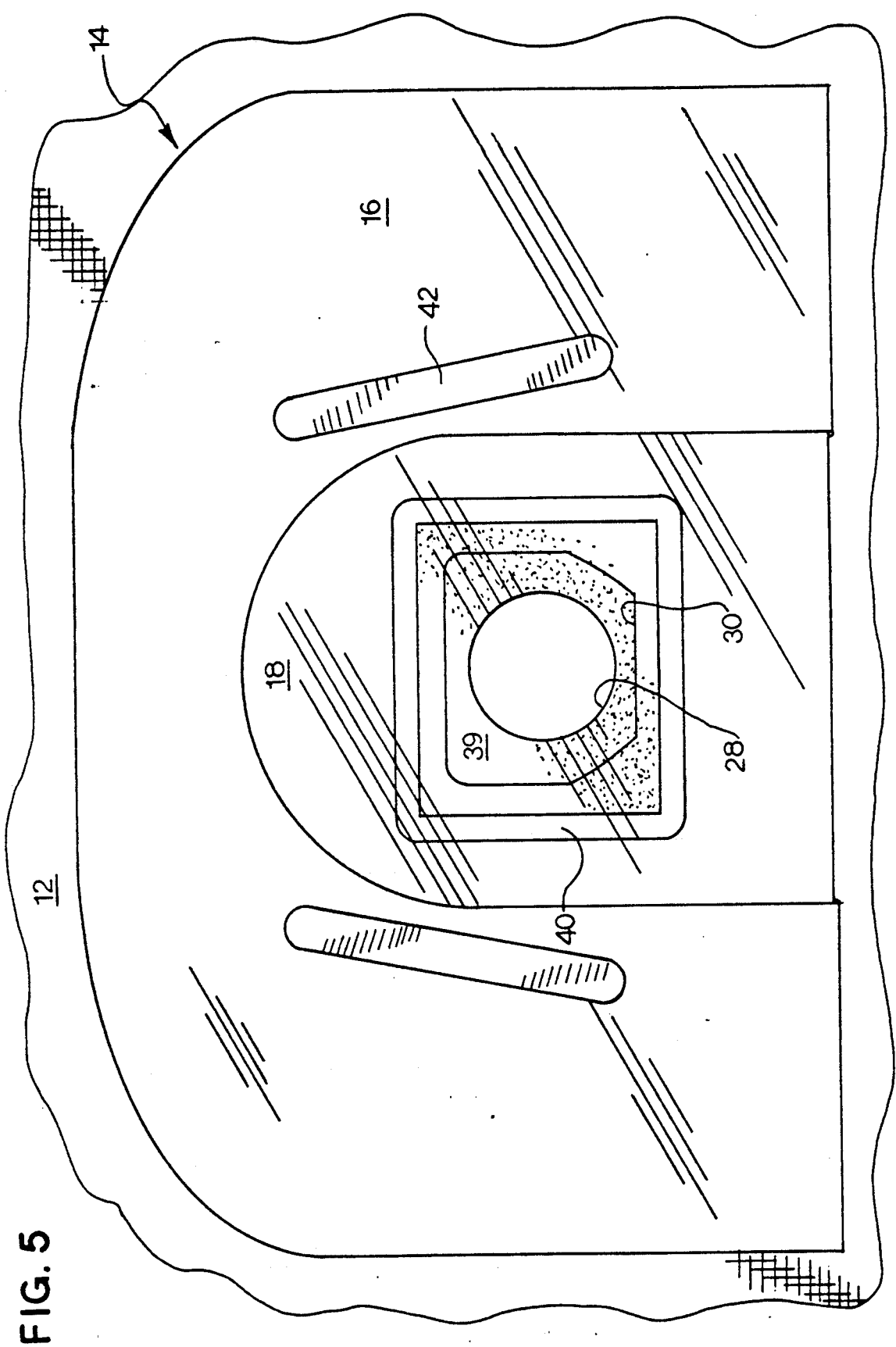
FIG. 5 illustrates an enlarged top elevational view of the fluid pouch on the surgical drape.

Referring to FIG. 1, the ophthalmic drape of the present invention, generally illustrated as 10, is draped over a patient undergoing an ophthalmic or other surgical procedure to contain fluids, such as body fluids and irrigation fluids, that collect during the course of the procedure. The ophthalmic drape 10 comprises a main sheet 12 which is substantially rectangular in shape and a fluid pouch 14.

The main sheet 12 may be made from a woven reusable fabric, but preferably is made from a nonwoven disposable fabric. The main sheet 12 should be large enough to cover the majority of the patient's body. In a preferred embodiment, the main sheet 12 is 71 inches wide by 108 inches long.

The main sheet 12 includes a fenestration 30 positioned approximately 30 inches from one end of the drape to be placed over the patient's operative eye. The surgical procedure will be performed within the main sheet fenestration 30.

The fluid pouch 14 includes a fluid collection portion 20 and an incise insert 21. The fluid collection portion 20 is made of a fluid impervious material, preferably a translucent plastic film such as polyethylene having a micro embossed surface.

The fluid collection portion 20 may be formed from a single piece of polyethylene material which is folded along a fold line 22 to form a top layer 16 and bottom layer 18. The curved outer edges 24 of the top layer 16 and bottom layer 18 are then heat sealed to form a collection area to collect the fluid run off from the surgical procedure. In its finished form the preferred embodiment of the fluid collection portion 20 is approximately 20 inches by 13 inches.

The top layer 16 of the fluid collection portion has a large cutaway 26 that extends to the fold line 22. The bottom layer 18 of the fluid collection portion has an approximately square shaped opening 32 surrounding by a textured reinforcement area 40 which reduces tearing of the pouch from the base sheet.

An incise insert is positioned within the bottom layer opening. Incise is a low density polyethylene film with adhesive on one side. The incise insert 21 adheres to the opening 32 of the bottom layer, and is positioned around and over the main sheet fenestration 30 to adhere the fluid pouch 14 to the main sheet 12. The incise insert 21 includes an incise fenestration or pouch fenestration 28 that is smaller than and concentric with the main sheet fenestration 30. Thus the incise insert 21 also adheres the drape 10 to the patient around the surgical site when the ophthalmic drape assembly is placed on the patient. A release layer 46 covers the adhesive on the inner portion 39 of the incise insert 21 prior to the drape being placed on the patient. After the release layer 46 is removed, the incise inner portion 39 is exposed through the main sheet fenestration 30 and will contact the patient when the drape 10 is placed on the patient. The incise insert fenestration 28 is sized to be placed around the patient's operative eye so that the surgical procedure can be performed within the fenestration 28.

The cutaway 26 on the fluid pouch or fluid collection portion top layer 16 is substantially larger than either the main sheet fenestration 30 or the incise insert fenestration 28. The cutaway 26 extends from the fold line 22 across the fenestrations 28 and 30 to within a few inches from the outer edge of the fluid pouch. The cutaway 26 exposes a portion of the fluid pouch bottom layer 18 in addition to the incise and incise fenestration 28.

When ophthalmic drape 10 is in use, the drape 10 is positioned so that the fenestration 28 is placed around the operative eye, with the outer edge 24 of the fluid pouch hanging downwards around the sides and top of the patient's head, as shown in FIG. 1. The top layer 16 of fluid pouch 14 hangs in a substantially vertical position so that fluid may collect in the pouch.

The drape 10 also includes two adjustment tabs 42 and a adjustment bar 44. Both the tabs 42 and the bar 44 are made of aluminum and have adhesive on one side to adhere to the drape or pouch and vinyl on the side facing away from the drape.

The two metal adjustment tabs 42 are positioned on the top layer 16 and may be folded to gather the corner of the top layer 16, allowing the fluid collecting portion 20 to lay relatively flat against the patient's head or wrist rest, even when the fluid collecting portion is filled with fluid. This reduces the splashing of fluids from the pouch.

The metal adjustment bar 44 is positioned on main sheet 12 adjacent to, but spaced apart from, fold line 22 of fluid pouch 14. Adjustment strip 44 may be folded to cause main sheet 12 to stand away from the patient's face to allow for easier patient breathing.

The drape 10 additionally comprises a cord holding tab 48 positioned between the adjustment bar 44 and the foot end 52 of the drape 10. In the preferred embodiment the tab 48 is four inches square and is positioned twelve inches from the adjustment bar 44. The tab 48 has two holes 50 adjacent one another on one end of the tab. The tab 48 is secured by adhesive to the main sheet on the opposite end of the tab. When the drape 10 is in use, tubing will be threaded through the holes 52 and the tab 48 twisted to hold the tubing in place against the drape and out of the way of the surgeon.

It should be understood that various changes and modifications to the preferred embodiment described herein will be apparent to those skilled in the art. Such changes and modifications can be made without departing from the spirit and scope of the present invention and without diminishing its intended advantages. It is therefore intended that such changes and modifications be covered by the appended claims.

I claim:

1. A surgical drape for placement on a patient, the drape comprising:
    a main sheet of an absorbent material, the main sheet having a fenestration of a predetermined size;
    a fluid collection pouch of a flexible fluid impervious material, the pouch having a fenestration of a second predetermined size smaller than the main sheet fenestration, the pouch having a top layer and a bottom layer, the pouch bottom layer having an outer side facing the main sheet, the pouch being positioned on the main sheet such that the pouch fenestration is substantially within the main sheet fenestration;
    an adhesive layer on at least a portion of the outer side of the pouch bottom layer, the adhesive layer substantially surrounding the pouch fenestration, the adhesive layer adhering the pouch to the main sheet adjacent the main sheet fenestration and to the patient upon the drape being positioned on the patient.

2. A surgical drape as claimed in claim 1, wherein the pouch substantially surrounds three sides of the main sheet fenestration.

3. A surgical drape as claimed in claim 2, wherein the pouch top layer and bottom layer are joined by a fold line.

4. A surgical drape as claimed in claim 1, wherein the pouch comprises a fluid collection portion and an insert, the fluid collection portion substantially surrounds the insert and wherein the adhesive layer is located on the insert.

5. A surgical drape as claimed in claim 4, wherein upon the drape being placed on the patient, the pouch fenestration registers about a patient's eye.

6. A surgical drape as claimed in claim 1, wherein the pouch top layer comprises a cutaway larger than the main sheet fenestration.

7. A surgical drape as claimed in claim 1, additionally comprises a release liner covering that portion of the adhesive layer inside the main sheet fenestration.

8. A surgical drape for ophthalmic procedures comprising:
    a main sheet having a fenestration;
    a fluid collection pouch of a fluid impervious material, the pouch comprising:
    a fluid collection portion having a top layer and a bottom layer joined by a fold line, the top layer having a cutaway larger than the main sheet fenestration, the bottom layer having an opening larger than the main sheet fenestration;
    an insert positioned within the bottom layer opening, the insert having an adhesive layer facing the main sheet, the adhesive layer adhering the insert to the main sheet, the insert to the fluid collection portion, and to insert to the patient when the drape is placed on the patient.

9. A surgical drape as claimed in claim 8, wherein the insert additionally comprises a fenestration smaller than the main sheet fenestration.

10. A surgical drape as claimed in claim 9, wherein the top layer cutaway is larger than the insert.

11. A surgical drape as claimed in claim 8, wherein the fluid collection portion is translucent.

12. A surgical drape as claimed in claim 9, wherein the insert fenestration is adapted to register about a patient's eye when the drape is placed on a patient.

13. A surgical drape for placement on a patient, said drape comprising:
   a main sheet having a fenestration;
   a fluid collection pouch of a fluid imperious material smaller than the main sheet fenestration, the pouch having a top layer and a bottom layer, the pouch bottom layer having a fenestration and an outer side facing the said main sheet, the pouch fenestration being smaller than and substantially concentric with the main sheet fenestration;
   an adhesive layer between a portion of the outer side of the pouch bottom layer and the main sheet and between the outer side of the pouch bottom layer and the patient upon the drape being positioned on the patient.

14. A surgical drape as claimed in claim 13, wherein said pouch substantially surrounds three sides of said main sheet fenestration.

15. A surgical drape as claimed in claim 13, wherein said pouch top layer and bottom layer are joined by a fold line.

* * * * *